United States Patent [19]

Scheffer et al.

[11] Patent Number: 5,073,661
[45] Date of Patent: Dec. 17, 1991

[54] PROCESS FOR THE PREPARATION OF HYDROCARBONS

[75] Inventors: Bob Scheffer; Andras G. T. G. Kortbeek, both of Amsterdam, Netherlands

[73] Assignee: Shell Oil Company, Houston, Tex.

[21] Appl. No.: 638,882

[22] Filed: Dec. 19, 1990

[51] Int. Cl.$^5$ ................................................ C07C 1/00
[52] U.S. Cl. .................................... 585/640; 585/733
[58] Field of Search ................................ 585/640, 733

[56] References Cited

U.S. PATENT DOCUMENTS

| | | | |
|---|---|---|---|
| 4,568,663 | 2/1986 | Mauldin | 502/325 |
| 4,663,305 | 5/1987 | Mauldin et al. | 502/304 |
| 4,670,475 | 6/1987 | Mauldin | 518/715 |
| 4,751,345 | 6/1988 | Mauldin | 585/733 |
| 4,885,405 | 12/1989 | Dornhagen et al. | 585/640 |

FOREIGN PATENT DOCUMENTS

| | | |
|---|---|---|
| 0178008 | 4/1986 | European Pat. Off. . |
| 0221598 | 5/1987 | European Pat. Off. . |
| 1548468 | 7/1979 | United Kingdom . |
| 2125062A | 2/1984 | United Kingdom . |
| 2130113A | 5/1984 | United Kingdom . |
| 2140701A | 12/1984 | United Kingdom . |
| 2153250A | 8/1985 | United Kingdom . |
| 2161177A | 1/1986 | United Kingdom . |
| 2161716A | 1/1986 | United Kingdom . |
| 2164266A | 3/1986 | United Kingdom . |

*Primary Examiner*—Curtis R. Davis
*Assistant Examiner*—E. D. Irzinski
*Attorney, Agent, or Firm*—Ronald R. Reper

[57] ABSTRACT

The invention relates to a process for the preparation of hydrocarbons, wherein a feed comprising methanol is contacted at reaction conditions with a catalyst comprising:

(i) a porous carrier material selected from the group comprising silica, alumina, and mixtures thereof;
(ii) cobalt as a metal component deposited on the porous carrier material; and
(iii) a promoter selected from the group comprising zirconium, titanium, chromium, ruthenium, iron, magnesium, zinc, thorium and uranium.

19 Claims, No Drawings

PROCESS FOR THE PREPARATION OF HYDROCARBONS

BACKGROUND OF THE INVENTION

The invention relates to a process for the preparation of hydrocarbons in a catalytic reaction at elevated temperature and pressure employing a methanol-comprising feed.

The preparation of hydrocarbons from a mixture comprising hydrogen and carbon monoxide, by contacting this mixture at elevated temperature and pressure with a specific catalyst, is known in the literature as the Fischer-Tropsch hydrocarbon synthesis process. Catalysts used in the Fischer-Tropsch synthesis process usually contain one or more metals from the iron group together with one or more promotors, both deposited on a porous carrier material. The products that can be prepared using these catalysts usually have a very wide range of molecular weight distribution, a large variety in branched and unbranched paraffins, and often contain considerable amounts of olefins and oxygen-containing organic compounds. Usually, only a minor portion of these products comprise so-called middle distillates. Middle distillates relate to hydrocarbon mixtures of which the boiling point range corresponds substantially to that of kerosine and gas oil fractions obtained in a conventional atmospheric distillation of crude mineral oil. The boiling point range of middle distillates generally lies within the range of about 150° to about 360° C. Furthermore, these middle distillates are obtained at a relatively low yield while their pour point is also unsatisfactory. Accordingly, the Fischer-Tropsch hydrocarbon synthesis process is not a very attractive direct route for the production of middle distillates on a technical scale.

Recently, Fischer-Tropsch catalysts have been found, which comprise cobalt as the metal component originating from the iron group, and a promotor. Suitable promotors are zirconium, titanium, chromium, ruthenium, iron, magnesium, zinc, thorium and uranium, preferably are zirconium, titanium, chromium and ruthenium and mixtures thereof, most preferably zirconium and titanium. More in particular, these catalyst comprise
i) a porous carrier material selected from the group comprising silica, alumina, and mixtures thereof;
ii) cobalt as a metal component deposited on the porous carrier material; and
iii) a promotor selected from the group comprising zirconium, titanium, chromium, ruthenium, iron, magnesium, zinc, thorium and uranium.

These catalyst yield a product in which only very minor amounts of olefins and oxygen-containing organic compounds are present and which consists substantially completely of unbranched paraffins. A considerable portion of these paraffins boil above the boiling point range of the middle distillates. It has been found that these high boiling portions of this product may be converted at high yields into middle distillates by means of hydrocracking. As a feedstock for hydrocracking at least a portion of the product is chosen such that the initial boiling point lies above the final boiling point of the heaviest middle distillates desired as end product. Hydrocracking typically proceeding at very low hydrogen consumption, yields middle distillates having a considerably better pour point than those obtained by the direct conversion according to the Fischer-Tropsch hydrocarbon synthesis process.

In the preparation of hydrocarbons, mixtures of hydrogen and carbon monoxide in molar ratios varying between about 0.5–3, are used in the Fischer-Tropsch hydrocarbon synthesis process.

Recently, it has been found that a specific type of Fischer-Tropsch catalyst may be used for the conversion of a feed comprising methanol and optionally a mixture of hydrogen and carbon monoxide into hydrocarbons. These specific catalysts, disclosed in U.S. Pat. Nos. 4,568,663; 4,663,305; and 4,751,345 are titania supported cobalt catalysts, promoted with rhenium, rhenium and thorium, zirconium, hafnium, cerium or uranium. It appears that in such processes employing methanol as feed, the selectivity for products with 2 or more carbon atoms is less than 75%.

Surprisingly, it has been found that the above-indicated class of Fischer-Tropsch catalysts comprising silica, alumina, or mixtures thereof shows a high selectivity for heavy hydrocarbons and is therefore especially suitable for the preparation of very heavy hydrocarbons which heavy hydrocarbons are very suitable for the production of middle distillates in a two-step process.

SUMMARY OF THE INVENTION

Accordingly, the invention relates to a process for the preparation of hydrocarbons, wherein a feed comprising methanol is contacted at reaction conditions with a catalyst comprising:
i) a porous carrier material selected from the group comprising silica, alumina, and mixtures thereof;
ii) cobalt as a metal component deposited on the porous carrier material; and
iii) a promotor selected from the group comprising zirconium, titanium, chromium, ruthenium, iron, magnesium, zinc, thorium and uranium.

DETAILED DESCRIPTION OF THE INVENTION

The preferred amounts of cobalt and promotor on the porous carrier material are among other things dependent on the method by which cobalt and the promotor are deposited on the carrier material. These deposition methods comprise precipitation, impregnation, kneading, melting, comulling and extrusion, and combinations thereof.

Suitably, the amount of cobalt is about 3–300 parts by weight per 100 parts by weight carrier material. When cobalt is deposited by impregnation and/or kneading, the amount of cobalt is suitably 5–60, preferably 20–50 parts by weight per 100 parts by weight carrier material. However, when cobalt is incorporated via an extrudable mixture with an extrudable carrier material precursor, the amount of cobalt is suitably 25–200 parts by weight, preferably 40–100 parts by weight, most preferably 50–100 parts by weight per 100 parts by weight of the carrier material.

The same applies to the amount of promotor present in the catalyst. Suitably, the catalyst comprises the promotor in an amount of 0.01–100 parts by weight per 100 parts by weight carrier material. If during the preparation of the catalyst first cobalt is deposited on the carrier material, and thereafter the promotor, the catalyst comprises suitably 0.1–5 preferably 0.25–5 parts by weight promotor per 100 parts by weight carrier material. If in the reverse mode of preparation the promotor is deposited first on the carrier and thereafter cobalt, the promotor is suitably present on the carrier material in an amount of 5-50 preferably 5-40 parts by weight per 100 parts by weight carrier material.

The carrier material to be used is preferably silica.

The promotor to be used is preferably zirconium or titanium, more preferably zirconium.

With respect to the various preparation modes of the catalyst reference is made to British Patent Application No. 2,140,701, reporting that an optimum catalyst performance in terms of activity and stability is obtained when the catalyst has such L and S as to satisfy the relation $$(3+4R) > L/S > (0.3+0.4),$$

wherein the various symbols have the following meanings:
L = the cobalt load present on the catalyst, expressed as mg Co/ml catalyst
S = the surface area of the catalyst expressed as m²/ml catalyst, and
R = the weight ratio of the amount of cobalt deposited on the catalyst by kneading to the total quantity of cobalt present of the catalyst.

The catalyst may be prepared from an extrudate, using a cobalt source convertible into the cobalt metal component of the final catalyst, which extrudate was formed by preparing an extrudable mixture of a carrier material precursor, a cobalt source and a solvent, comulling the mixture, extruding the mixture comulled and drying the formed extrudate. Specifically, alumina is used as the carrier material precursor. Optionally, the extrudable mixture may comprise further a promotor source, which means that this promotor source is convertible in the promotor present in the final catalyst product.

In another extrusion embodiment for the catalyst for use in the process according to the invention, the catalyst is formed by preparing an extrudable mixture of a carrier material precursor, a promotor source and a solvent, comulling the mixture, extruding the mixture comulled and drying the formed extrudate, whereafter cobalt is deposited on the extrudate by for instance precipitation and impregnation.

The texture of the catalyst may be of importance for the activity and selectivity in the catalytic conversion process. As indicated in British Patent No. 1,548,468, these catalysts have an excellent activity and selectivity if the ratio of the specific average pore diameter (p in nm) over the specific average particle diameter (d in mm), is larger than 2.0.

The carrier material provided with both cobalt and promotor is usually subjected to calcination at a temperature of suitably 350°-750° C., preferably a temperature in the range of 450°-550° C. in order to remove crystal water and to decompose organic and inorganic compounds to oxides and volatile decomposition products. If the calcination is carried our under specific conditions, the activity and selectivity of the catalysts may be further improved. Accordingly, the calcination is preferably performed in an atmosphere containing nitrogen oxide, whereas the cobalt precursor suitably consists of cobalt nitrate. More specifically, the calcination is suitably performed in an atmosphere containing nitrogen oxide in a concentration of at least 20% by volume taking the water content of the atmosphere not into consideration.

This specific calcination treatment results in the formation of cobalt oxide containing agglomerates having a size of about 1-10 microns.

Finally, the catalyst may be activated by contacting the catalyst with hydrogen or a hydrogen containing gas t a temperature of 200°-250° C., preferably 250°-300° C. British Patent Application No. 2,161,716 discloses that the catalyst performance is improved when the activation is performed under a hydrogen partial pressure between 0.001 and 75 bar and during the activation the hydrogen partial pressure is increased gradually or step-wise from an initial value $(P_{H2})_i$ to an ultimate value $(P_{H2})_u$ in such a manner as to satisfy the relation $(P_{H2})_u > 5 \times (P_{H2})_i$. Furthermore, British Patent Application No. 2,153,250 discloses that optimum catalyst results are obtained if the activation is performed under such conditions as to satisfy the relation:

$$\frac{D}{10^4 \times (P_{H2})^2 \times P_{Tot}} > \frac{10 \times S}{L \times (Z+1)}$$

wherein
D = space velocity, as Nl/l.h
$P_{H2}$ = hydrogen partial pressure, as bar,
$P_{Tot}$ = overall pressure, as bar,
S = surface area of the catalyst, as m²/ml,
L = cobalt load of the catalyst, as mg Co/ml, and
Z = zirconium load of the catalyst, a mg Zr/100 mg carrier material.

Suitable catalysts for the conversion of methanol-comprising feed into liquid hydrocarbons are disclosed in British Patent No. 1,548,468; and in British Patent Application Nos. 2,125,062; 2,130,113; 2,140,701; 2,153,250; 2,161,177; 2,164,266; 2,161,716; and European Patent Application Nos. 178,008; and 221,598.

The catalysts are preferably used in the form of spherical, cylindrical or lobed particles having a nominal diameter of 0.5-5 mm, preferably 1-2 mm The preparation of hydrocarbons from a feed comprising methanol, methanol and hydrogen, or methanol and synthesis gas is generally performed at a temperature between 100° and 600° C., such as 150°-300° C., preferably 180°-270°, most preferably 200°-250° C., at a total pressure of generally 1-200 bar absolute, preferably 10-70 bar absolute. The space velocity is about 200°-20,000 m³ (STP) gaseous feed/m³ reaction zone/hour. The term "STP" used herein means Standard Temperature (of °C.) and Pressure (of 1 bar absolute). Preferably the feed comprises methanol and hydrogen in a molar ratio of 4:1 to 60:1, preferably 8:1 to 30:1. It may be advantageous that the feed comprises methanol and synthesis gas.

A preferred embodiment of the process according to the invention consists in that the preparation of hydrocarbons from methanol is used as the first step in a two-step process for the preparation of middle distillates.

To this end the hydrocarbons product, or at least that part of the product which has an initial boiling point above the final boiling point of the desired middle distillate fraction, is subjected to a catalytic hydrotreatment as the second step in the process.

The catalytic hydrotreatment is suitably carried out by contacting the hydrocarbon material from the first step at elevated temperatures and pressures and in the presence of hydrogen with a catalyst comprising one or more metals having hydrogenation activity, supported on a carrier.

In the hydrotreatment preference is given to the use of a catalyst comprising one or more metals from Group VIII, supported on a carrier. In particular, a catalyst is preferred comprising platinum on a carrier 13-15% w of which consists of alumina and the rest of silica. The preferred reaction conditions in the hydrotreatment are temperatures in the range of 175°-400° C., in particular of 250°-350° C., a hydrogen partial pressure of 1 to 25 MPa, in particular of 2.5 to 15 MPa, a space velocity of 0.1-5 kg/l.h, in particular of 0.25-2 kg/l.h and a hydrogen/oil ratio of 100-5000 Nl/kg, in particular of 250-2500 Nl/kg.

The invention will be illustrated hereafter by a practical example of the process of the invention for the conversion of methanol in hydrocarbons using a catalyst having an excellent $C_5+$ *selectivity*.

EXAMPLE

A catalyst was prepared using spherical silica carrier dried at 120° C. Thereafter the carrier particles were emerged in a solution of cobalt nitrate in water. The amount of solution used was such at its volume corresponded substantially to the pore volume of the carrier. The solution had a viscosity measured at 60° C. of 1.7 cSt. After drying and calcining at 500° C. the cobalt loaded silica carrier was dried and calcined at 500° C.

The catalyst prepared was reduced (260° C., 3 bar absolute), 6000 GHSV, in a gas stream comprising an increasing hydrogen concentration (1-100%).

Thereafter, the catalyst was contacted with methanol at the following test conditions: pressure 26 bar (absolute), 210° C. and 800 GHSV. The $C_5+$ selectively (% w on $C_{C1}+$) was more than 80%.

What is claimed is:

1. Process for the preparation of hydrocarbons, wherein a feed comprising methanol is contacted at reaction conditions with a catalyst comprising:
   i) a porous carrier material selected from the group comprising silica, alumina, and mixtures thereof;
   ii) cobalt as a metal component deposited on the porous carrier; and
   iii) a promotor selected from the group comprising zirconium, titanium, chromium, ruthenium, iron, magnesium, zinc, thorium and uranium.

2. Process as claimed in claim 1, wherein the catalyst comprises cobalt in an amount of 3-300 parts by weight per 100 parts by weight carrier material.

3. Process as claimed in claim 2, wherein the amount of cobalt is 5-60 parts by weight per 100 parts by weight carrier material, when cobalt is deposited by precipitation, impregnation, melting and/or kneading.

4. Process as claimed in claim 2, wherein the amount of cobalt is 25-200 parts by weight per 100 parts by weight carrier material, when cobalt is incorporated via an extrusion process.

5. Process as claimed in claim 1, wherein the promotor is present in an amount of 0.01-100 parts by weight per 100 parts by weight carrier material.

6. Process as claimed in claim 5, wherein the promotor is present in an amount of 0.1-5 parts by weight by 100 parts by weight carrier material if during the preparation of the catalyst first cobalt is deposited on the carrier material, and thereafter the promotor.

7. Process as claimed in claim 5, wherein the promotor is present in an amount of 5-50 parts by weight per 100 parts by weight carrier material if the promotor is deposited first on the carrier and thereafter cobalt.

8. Process as claimed in claim 1, wherein the catalyst has such L and S as to satisfy the relation $$L > (0.3 + 0.4R), > L/S > (0.3 + 0.4R),$$

wherein the various symbols have the following meanings:
L = the cobalt load present on the catalyst, expressed as mg Co/ml catalyst,
S = the surface area of the catalyst expressed as m²/ml catalyst, and
R = the weight ratio of the amount of Cobalt deposited on the catalyst by kneading to the total quantity of cobalt present of the catalyst.

9. Process as claimed in claim 1, wherein the catalyst has been prepared from an extrudate formed by preparing an extrudable mixture of a carrier material precursor, a cobalt source and a solvent, comulling the mixture, extruding the mixture comulled and drying the formed extrudate.

10. Process as claimed in claim 9, wherein the mixture to be comulled comprises further a promotor source.

11. Process as claimed in claim 9, wherein the catalyst has been calcined at a temperature of 350°-750° C.

12. Process as claimed in claim 1, wherein the catalyst has been formed by preparing an extrudable mixture of a carrier material precursor, a promotor source and a solvent, comulling the mixture, extruding the mixture comulled and drying the formed extrudate.

13. Process as claimed in claim 12, wherein the catalyst has been calcined at a temperature of 350°-750° C.

14. Process as claimed in claim 1, wherein cobalt has been deposited on the carrier material as cobalt nitrate and the catalyst has been calcined in an atmosphere containing nitrogen oxide in a concentration of at least 20% by volume, taking the water content of the atmosphere not into consideration.

15. Process as claimed in claim 1, wherein the catalyst has been activated by contacting the catalyst with hydrogen or a hydrogen containing gas at a temperature of 200°-350° C.

16. Process as claimed in claim 1, which is carried out at 150°-350° C.

17. Process as claimed in claim 1, which is carried out at a pressure of 10-70 bar.

18. Process as claimed in claim 1, wherein the feed comprises methanol and hydrogen in a molar ratio of 4:1 to 60:1.

19. Process as claimed in claim 1, wherein the feed comprises methanol and synthesis gas.

* * * * *

UNITED STATES PATENT AND TRADEMARK OFFICE
CERTIFICATE OF CORRECTION

PATENT NO. : 5,073,661
DATED      : December 17, 1991
INVENTOR(S) : Bob Scheffer and Andras G.T.G. Kortbeek It is certified that error appears in the above-identified patent and that said Letters Patent is hereby corrected as shown below:

On cover page after the filing date, item (22), insert the following:

(30)    Foreign application priority data

May 4, 1990 (GB)   United Kingdom ........9010076

Signed and Sealed this

Thirtieth Day of March, 1993

*Attest:*

STEPHEN G. KUNIN

*Attesting Officer*      Acting Commissioner of Patents and Trademarks